(12) United States Patent
Lauf et al.

(10) Patent No.: US 11,903,624 B2
(45) Date of Patent: Feb. 20, 2024

(54) ORTHOPEDIC IMPLANTS WITH VARIABLE ANGLE BONE SCREW LOCKING

(71) Applicant: Life Spine, Inc., Huntley, IL (US)

(72) Inventors: Garrett D. Lauf, Elgin, IL (US); Paul C. Zakelj, Chicago, IL (US); Matthew S. Coyne, Naperville, IL (US)

(73) Assignee: Life Spine, Inc., Huntley, IL (US)

( * ) Notice: Subject to any disclaimer, the term of this patent is extended or adjusted under 35 U.S.C. 154(b) by 205 days.

(21) Appl. No.: 17/204,575

(22) Filed: Mar. 17, 2021

(65) Prior Publication Data
US 2021/0196330 A1 Jul. 1, 2021

Related U.S. Application Data

(62) Division of application No. 15/256,679, filed on Sep. 5, 2016, now Pat. No. 10,966,765.
(Continued)

(51) Int. Cl.
*A61B 17/80* (2006.01)
*A61B 17/86* (2006.01)
*A61B 17/70* (2006.01)

(52) U.S. Cl.
CPC ...... *A61B 17/8047* (2013.01); *A61B 17/7059* (2013.01); *A61B 17/80* (2013.01);
(Continued)

(58) Field of Classification Search
CPC ............ A61B 17/8033; A61B 17/8047; A61B 17/8052; A61B 17/861; A61B 17/8695
See application file for complete search history.

(56) References Cited

U.S. PATENT DOCUMENTS

| | | | | |
|---|---|---|---|---|
| 3,596,656 A | * | 8/1971 | Kaute | A61B 17/746 411/908 |
| 5,531,746 A | * | 7/1996 | Errico | A61B 17/8004 606/287 |

(Continued)

FOREIGN PATENT DOCUMENTS

EP 2 008 599 A1 12/2008

OTHER PUBLICATIONS

Preliminary Report on Patentability for International Application No. PCT/US2016/050331, dated Mar. 6, 2018, 10 pages.
(Continued)

*Primary Examiner* — Anu Ramana
(74) *Attorney, Agent, or Firm* — Foley & Lardner LLP

(57) ABSTRACT

An orthopedic implant has a plate and bone screws. Configured bone screw pockets of the plate provide variable angling and positional locking of a received bone screw relative. Each bone screw includes distal threads, a neck, and a dual threaded head. The plate has a bone screw pocket on a distal end, a bone screw pocket on a proximal end, and a strut extending between the two bone screw pockets. The bone screw pockets are at least generally cup shaped for receipt of a bone screw. The lower periphery of the opening of each bone screw pocket has an arrangement of configured prongs with configured openings to receive threading on the underside of the dual threaded head of the bone screw. The prongs can preferably, but not necessarily, deform slightly and grab onto the threading of the bone screw head to lock the bone screw in the bone screw pocket. Each prong can act independently.

20 Claims, 16 Drawing Sheets

Related U.S. Application Data

(60) Provisional application No. 62/362,089, filed on Jul. 14, 2016, provisional application No. 62/261,053, filed on Nov. 30, 2015, provisional application No. 62/214,954, filed on Sep. 5, 2015.

(52) U.S. Cl.
CPC ...... *A61B 17/8052* (2013.01); *A61B 17/8057* (2013.01); *A61B 17/8605* (2013.01)

(56) References Cited

U.S. PATENT DOCUMENTS

| | | | |
|---|---|---|---|
| 5,976,141 A * | 11/1999 | Haag | A61B 17/8047 606/301 |
| 6,129,730 A | 10/2000 | Bono et al. | |
| 7,306,602 B2 * | 12/2007 | Bono | A61B 17/7035 606/292 |
| 7,682,379 B2 * | 3/2010 | Mathieu | A61B 17/8047 606/280 |
| 7,766,917 B2 * | 8/2010 | Kugler | A61B 17/92 606/86 R |
| 7,799,062 B2 * | 9/2010 | Crozet | A61B 17/8057 606/311 |
| 8,105,367 B2 | 1/2012 | Austin et al. | |
| 8,142,485 B2 * | 3/2012 | Buhren | A61B 17/8057 606/289 |
| 8,361,126 B2 * | 1/2013 | Perrow | A61B 17/8891 606/287 |
| 8,945,193 B2 | 2/2015 | Kirschman | |
| 8,951,291 B2 * | 2/2015 | Impellizzeri | A61B 17/8057 606/291 |
| 9,642,659 B2 * | 5/2017 | Velikov | A61B 17/8695 |
| 2006/0116679 A1 * | 6/2006 | Lutz | A61B 17/80 606/281 |
| 2008/0208259 A1 | 8/2008 | Gilbert et al. | |
| 2010/0241175 A1 | 9/2010 | Walker et al. | |
| 2010/0324604 A1 * | 12/2010 | Mathieu | A61B 17/8047 606/289 |
| 2011/0015681 A1 | 1/2011 | Elsbury | |
| 2011/0137314 A1 | 6/2011 | Kuster et al. | |
| 2011/0172666 A1 | 7/2011 | Heilman | |
| 2012/0136396 A1 | 5/2012 | Baker et al. | |
| 2013/0172943 A1 | 7/2013 | Austin et al. | |
| 2015/0112393 A1 | 4/2015 | Garber | |
| 2016/0235453 A1 * | 8/2016 | Biedermann | A61B 17/8061 |
| 2017/0238980 A1 | 8/2017 | Lauf et al. | |

OTHER PUBLICATIONS

Search Report and Written Opinion for International Application No. PCT/US2016/050331, dated Jan. 3, 2017, 10 pages.

* cited by examiner

ORTHOPEDIC IMPLANTS WITH VARIABLE ANGLE BONE SCREW LOCKING

CROSS-REFERENCE TO RELATED PATENT APPLICATIONS

This is a divisional of U.S. application Ser. No. 15/256,679, filed on Sep. 5, 2016, which claims the benefit of and/or priority under 35 U.S.C. § 119(e) to U.S. App. No. 62/214,954, filed on Sep. 5, 2015, U.S. App. No. 62/261,053, filed on Nov. 30, 2015, and U.S. App. No. 62/362,089, filed on Jul. 14, 2016, the entire contents of all such applications is specifically hereby incorporated herein by reference.

BACKGROUND

The present invention relates to artificial implants for orthopedics such as locking plates and screws and, particularly, to implants that allow variable angle locking of bone screws.

There are various reasons why surgical intervention may be required with respect to bones of the body. Bone issues such as trauma, disease, acquired or congenital deformity can necessitate the use of one or more orthopedic implant in order to mend, join, and/or fix one or more bones and/or bone portions of the body. One type of orthopedic implant consists of a plate and bone screws to attach the plate to the one or more bones or bone portions.

One issue with plate and screw type orthopedic implants is how to allow for angulation of an attachment bone screw in order to accommodate a patient's anatomy while positively fixing its position once installed. Another issue is how to prevent reverse rotation (back out) of the attachment bone screw once installed. A further issue is the need to minimize the number of components of the implant. While various plate and screw implants have been developed in an attempt to overcome these issues, they fall short of achieving the goal.

Given the above, it is an object of the present invention to provide an orthopedic implant that allows variable angle bone screw locking.

SUMMARY

The invention is an orthopedic implant characterized by a plate and bone screws, the plate providing variable angling and positional locking of a received bone screw relative to the plate. The present orthopedic implant is used to treat a wide variety of bone issues of the spine, foot, and hand, as well as other bones of the body.

Each bone screw includes distal threads, a neck, and a dual threaded head. They may be configured as both locking and non-locking.

The plate has a bone screw pocket on a distal end, a bone screw pocket on a proximal end, and a strut extending between the two bone screw pockets. The bone screw pockets are at least generally conical shaped, cup shaped, or the like to allow for receipt of both locking and non-locking bone screws. The lower periphery of the opening of each bone screw pocket has an arrangement of configured lips, tangs, projections, ledges, protrusions, or the like (collectively, lips) with configured cutouts, slots, openings or the like (collectively, slots) configured to receive threading on the underside of the dual threaded head of the bone screw. The lips can preferably, but not necessarily, deform slightly and grab onto the threading of the bone screw head to lock the bone screw in the bone screw pocket. Each lip can act independently.

In a form, the screw pockets have a plurality of equidistant cutouts that define a plurality of tangs. These tangs mesh with the threading of the bone screw, preventing it from moving. This locks the bone screw into position.

The variable angle locking screw and plate implant may include a third component, whereby the present orthopedic implant consists of three main components: an orthopedic plate; an insert preferably, but not necessarily made of PEEK; and a variable angle locking screw. The orthopedic plate has two screw pockets, each having an undercut that is used to capture the insert, and which is also keyed to prevent the insert from rotating. The insert is an annular member having a race, ledge or projection proximate the lower edge thereof that prevents the insert from dislodging from the screw pocket. The insert is also keyed to fit into the keyed screw pocket to prevent rotation. The screw includes distal threads, a neck, and a dual threaded head. While the screw is inserted, the threads on the head of the screw engage with the insert and lock the screw into the plate, preventing any further angulation. Other configurations of the pocket and/or insert that key the insert in the pocket or otherwise retains the insert into the pocket are contemplated.

Each lip of an arrangement of lips may have a generally blunt or flat end. In a form, each lip of an arrangement of lips has a generally rounded or curved end.

Other configurations are contemplated, as well as arrangements of lips of different end configurations.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE FIGURES

The components, features and functions of the present invention will be better understood by reference to the accompanying drawings which illustrate forms of the invention, wherein.

It should be appreciated that dimensions of the components, structures, and/or features of the present variable angle locking screw and plate implants may be altered or configured as desired while maintaining the principles of the invention.

DETAILED DESCRIPTION

Figure 1:
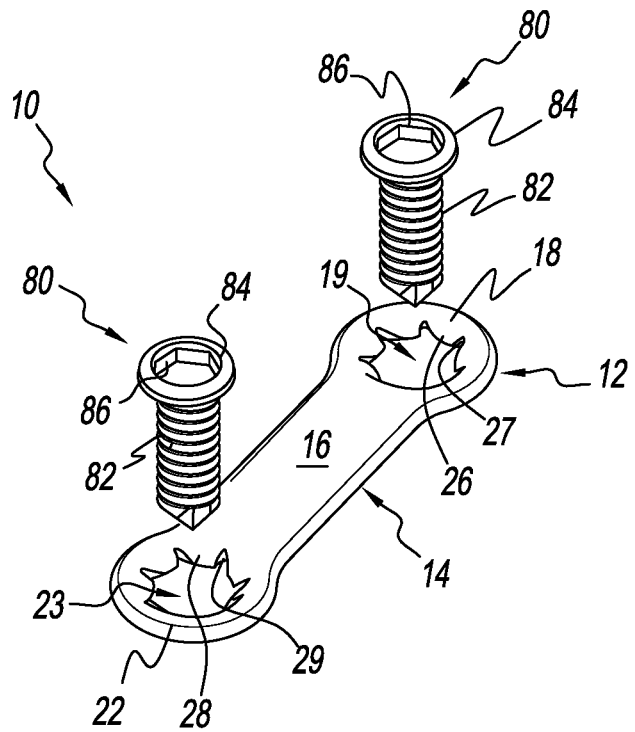
FIG. 1 is an exploded view of components of an orthopedic implant fashioned in accordance with the present principles.
Figure 2:
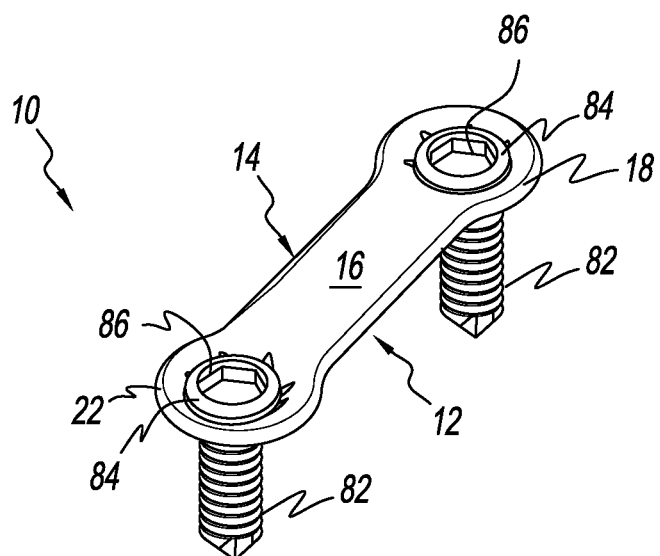
FIG. 2 is an isometric view of the orthopedic implant of FIG. 1, assembled.

Referring to FIGS. 1 and 2, there is depicted an exemplary form of the present orthopedic implant comprising a configured plate and variable angle locking screw implant, construct, device or the like, generally designated 10. The variable angle locking screw and plate implant (implant or orthopedic implant) 10 is made from a biocompatible material such as, but not limited to, titanium, stainless steel, an alloy of titanium or steel, or other biocompatible material. The implant 10 is designed for orthopedics use but other bodily uses are contemplated. FIG. 1 shows the two (2) components of the variable angle locking screw and plate implant 10 namely, a variable angle locking bone screw 80 and a plate 12, in an exploded state, while FIG. 2 depicts the components of the variable angle locking bone screw implant 10 in an assembled state.

Figure 3:
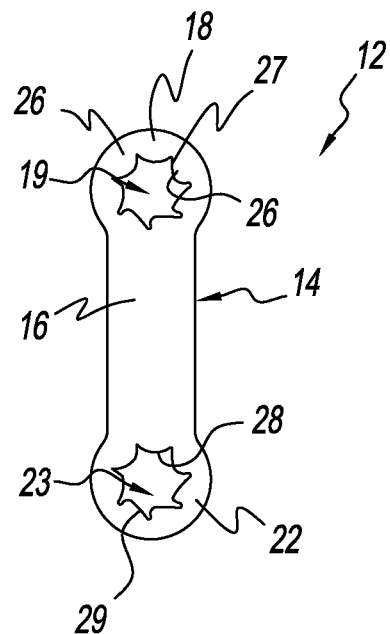
FIG. 3 is a top plan view of a plate component of the orthopedic implant of FIG. 1.
Figure 5:
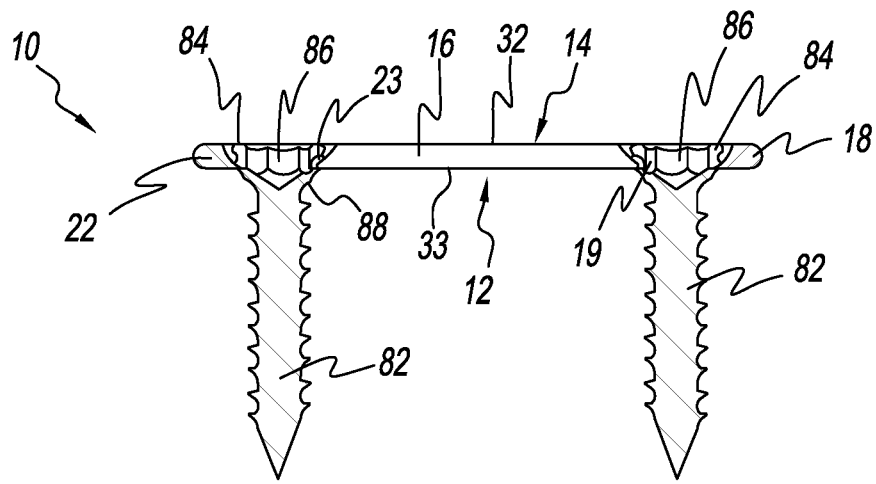
FIG. 5 is a sectional side view of the orthopedic implant of FIG. 1.

As seen in FIG. 3, the plate 12 is characterized by a generally elliptical body 14 having a first rounded end 18 and a second rounded end 22, the nomenclature first and second being arbitrary here and throughout. A strut 16 extends between the first rounded end 18 and the second rounded end 22. The body 14 is generally flat as best illustrated in FIG. 5 having a generally flat upper side 32 and lower side 33, but may have a curvature along the major axis or another long axis of the body 14 and/or along the minor axis or another short axis of the body 14. A first open pocket, configured opening, or the like 19 is provided in the first end 18, while a second open pocket, configured opening, or the like 23 is provided in the second end 22.

Figure 4:
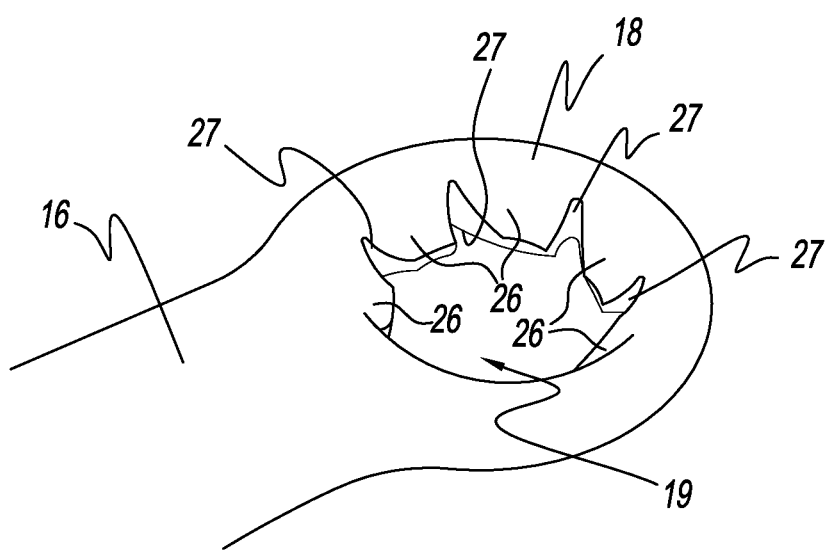
FIG. 4 is an enlarged view of one end of the plate of the orthopedic implant of FIG. 1.

The first pocket 19 (see, e.g., FIGS. 1 and 4-5) has a generally conical inlet with a plurality of cutouts, slots or the like 27 formed in the inlet sidewall of the pocket 19. The plurality of cutouts 27 define a plurality of tangs, ledges or the like 26. Preferably, but not necessarily, the cutouts are spaced equidistant from one another about the annular conical inlet, such that the formed tangs 26 are likewise equidistant from one another. Additionally, seven (7) cutouts and seven (7) are the currently preferred mode, but other numbers of cutouts and tangs both odd and even are contemplated to be used. The second pocket 23, (see, e.g., FIGS. 1, 5-6) likewise has a generally conical inlet with a plurality of cutouts, slots or the like 29 formed in the inlet sidewall of the pocket 23. The plurality of cutouts 29 define a plurality of tangs, ledges or the like 28. Preferably, but not necessarily, the cutouts are spaced equidistant from one another about the annular conical inlet, such that the formed tangs 28 are likewise equidistant from one another. Additionally, seven (7) cutouts and seven (7) are the currently preferred mode, but other numbers of cutouts and tangs both odd and even are contemplated to be used. Preferably, but not necessarily, the number of cutouts and tangs for each pocket 19, 23 are the same. These tangs mate with the dual thread of the bone screw 80 (as described below), preventing the bone screw 80 from moving, thus locking the bone screw 80 into position relative to the plate 12.

Figure 6:
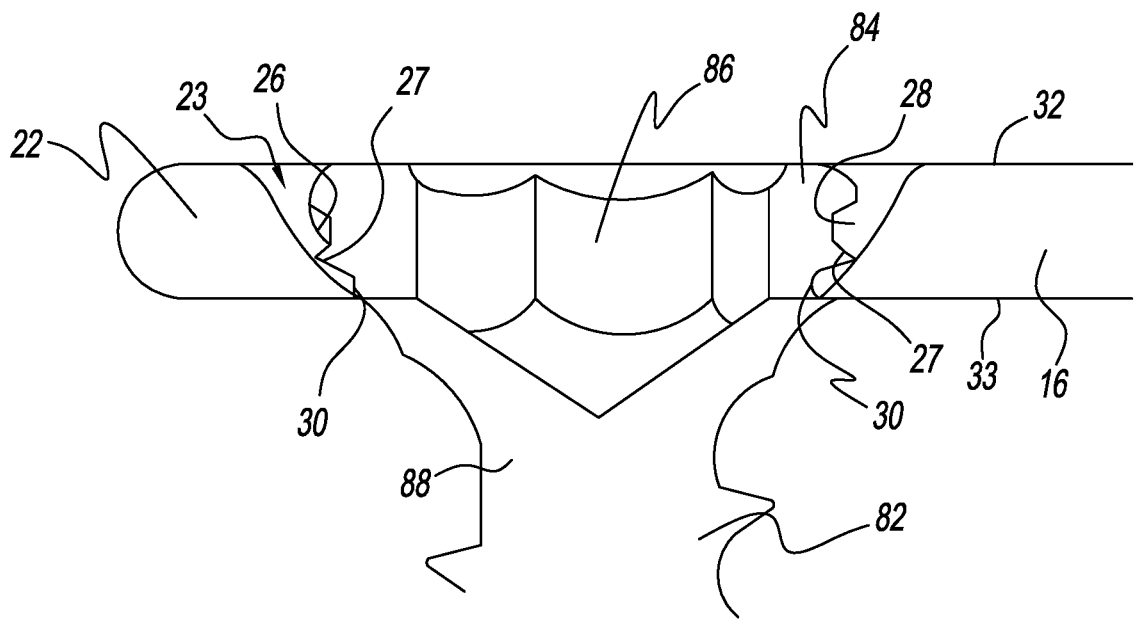
FIG. 6 is an enlarged view of one end of the sectional side view of FIG. 5.

The underside of each pocket 19, 23 is configured as shown in FIG. 6 where the underside 30 of the pocket 23 of the second end 22 is illustrated. The underside 30 is angled to receive threading of the bone screw 80. This aids in locking the angle and position of the bone screw 80 relative to the plate 12.

Figure 7:
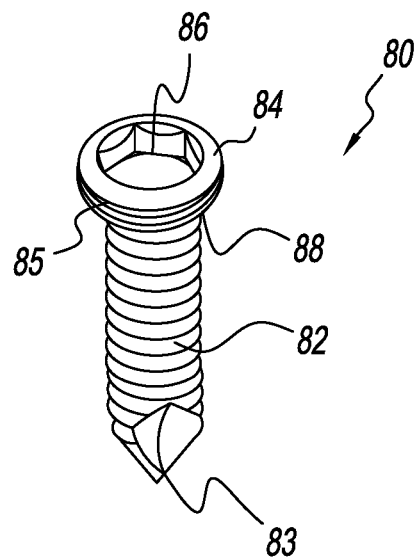
FIG. 7 is an isometric view of the variable angle locking screw of the orthopedic implant of FIG. 1.
Figure 8:
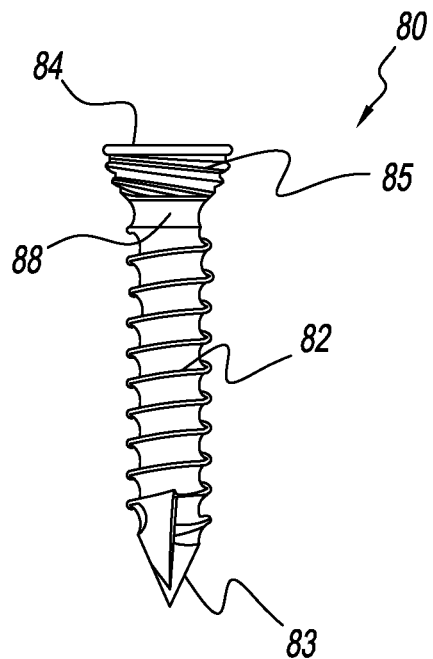
FIG. 8 is a side view of the variable angle locking screw of FIG. 7.

Referring to FIGS. 7 and 8, the variable angle locking bone screw 80 is shown. The variable angle locking bone screw 80 is characterized by a threaded shank 82 having a preferably, but not necessarily, pointed tip 83 at a distal end of the threaded shank 82, a neck 88 at a proximate end of the threaded shank 82, and a head 84 at the end of the neck 88. A socket 86 is provided in the top of the head 84 that is configured to receive a like configured driving tool (not shown). While the socket 86 is configured as a hexagon for receipt of a hexagon driving tool (not shown), other socket configurations and thus driver tools may be used. The underside of the head 84 has dual threads or threading 85. The dual threading underside 85 of the head 84 meshes and/or engages with the tangs of a pocket of the plate 12 to angularly position and fix the screw 80 relative to the plate 12.

Figure 9:
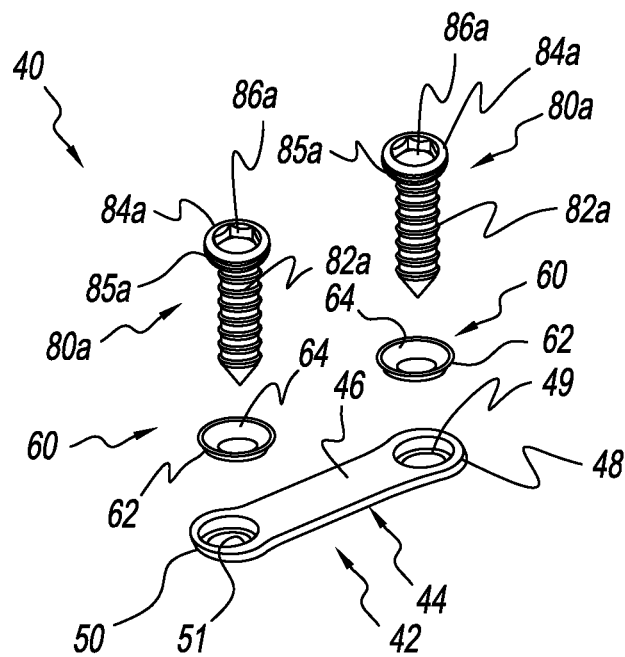
FIG. 9 is an exploded view of components of another orthopedic implant fashioned in accordance with the present principles.
Figure 10:
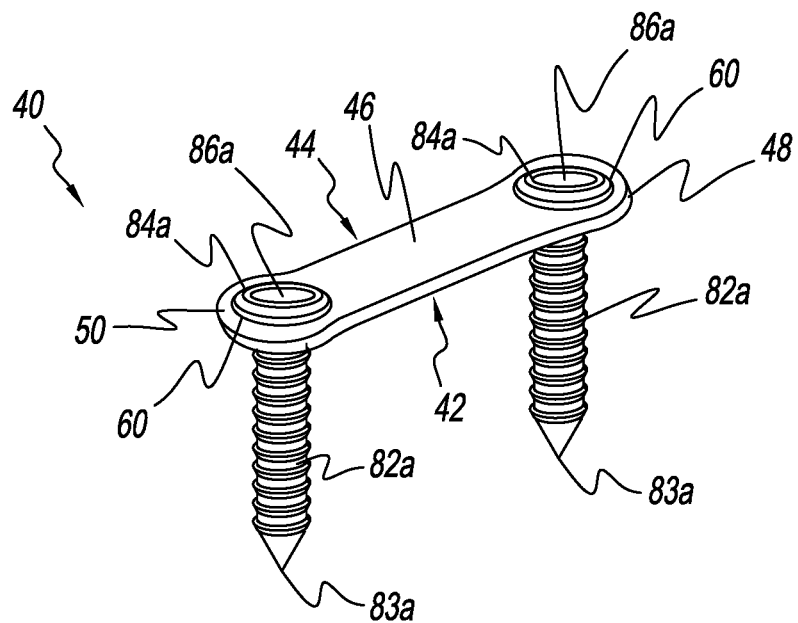
FIG. 10 is an isometric view of the orthopedic implant of FIG. 9, assembled.

Referring now to New FIGS. 9 and 10, there is depicted another exemplary form of the present orthopedic implant comprising a variable angle locking screw and plate implant, construct, device or the like, generally designated 40. The variable angle locking screw and plate implant 40 is made from a biocompatible material such as, but not limited to, titanium, stainless steel, an alloy of titanium or steel, or other biocompatible material. The implant 40 is designed for orthopedics use but other bodily uses are contemplated. FIG. 9 shows the three (3) different components of the variable angle locking screw and plate implant 40 namely, a variable angle locking bone screw 80, two identical inserts 60, and a plate 42, in an exploded state, while FIG. 10 depicts the components of the variable angle locking bone screw implant 40 in an assembled state.

Figure 11:
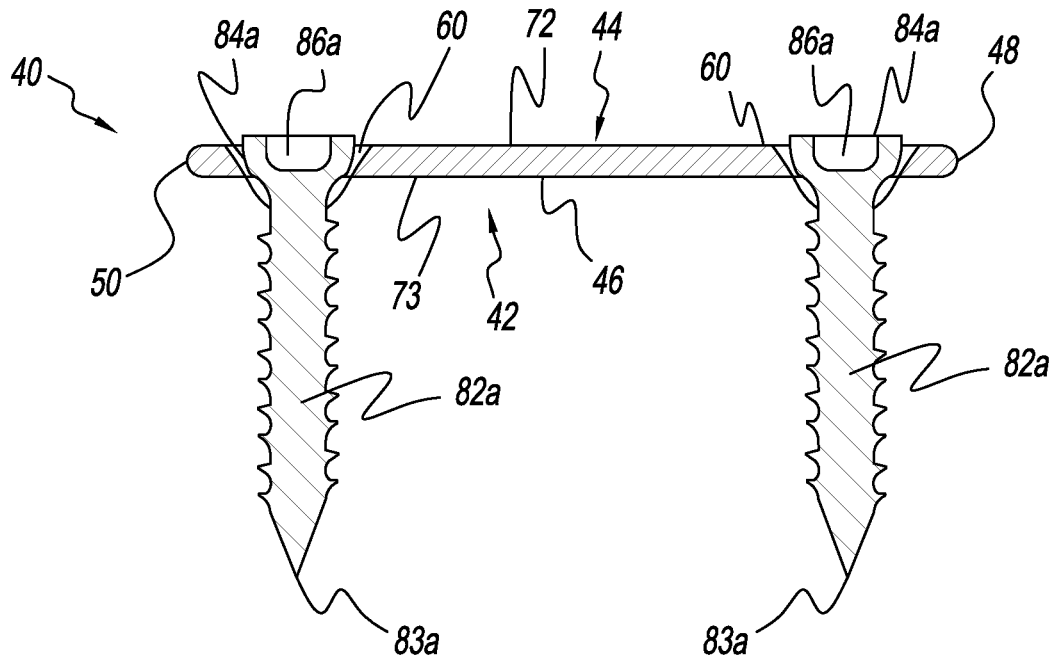
FIG. 11 is a sectional side view of the orthopedic implant of FIG. 9.
Figure 19:
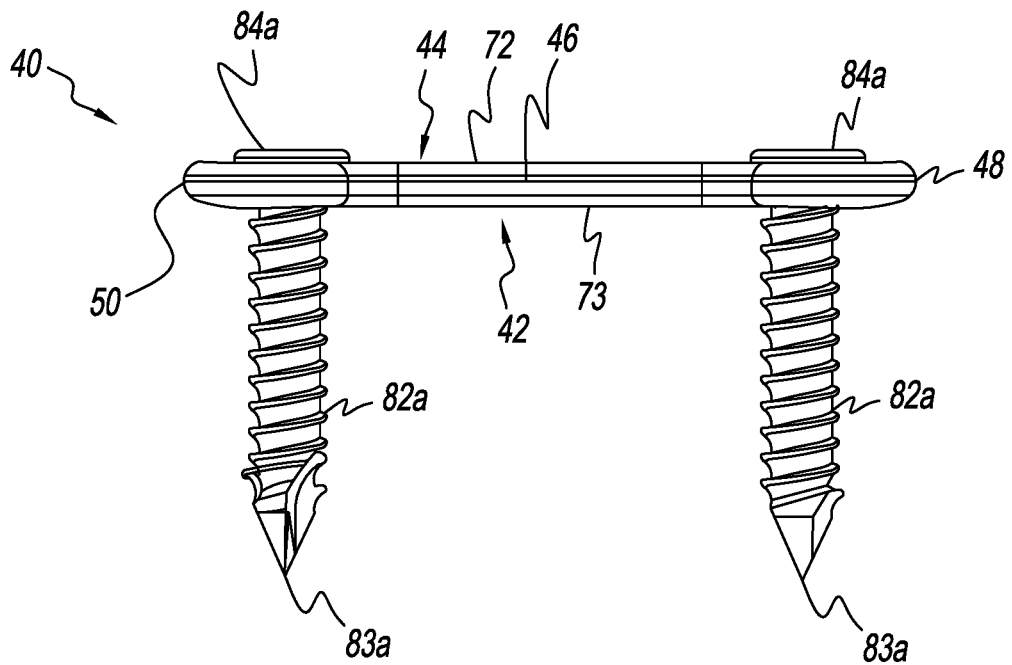
FIG. 19 is a side view of the assembled orthopedic implant of FIG. 9.
Figure 20:
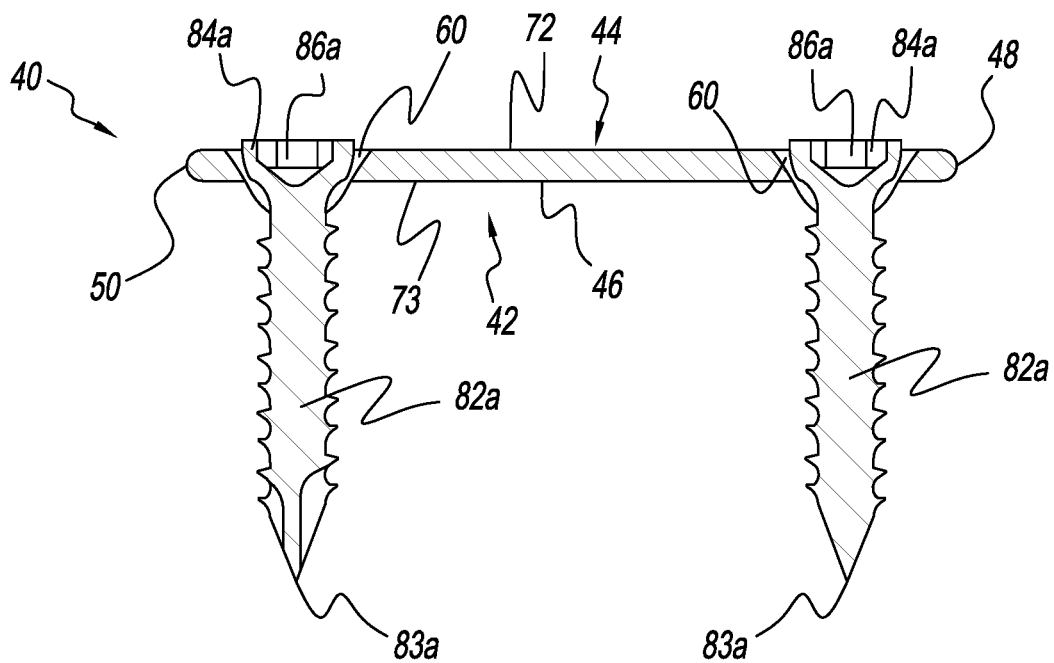
FIG. 20 is a sectional side view of the orthopedic implant of FIG. 19.

As seen in FIGS. 9 and 10, the plate 42 is characterized by a generally elliptical body 44 having a first rounded end 48 and a second rounded end 50, the nomenclature first and second being arbitrary here and throughout. A strut 46 extends between the first rounded end 48 and the second rounded end 50. The body 44 is generally flat as seen in FIGS. 11, 19, 20 having a generally flat upper side 72 and lower side 73, but may have a curvature along the major axis or another long axis of the body 44 and/or along the minor axis or another short axis of the body 44. A first open pocket, configured opening, or the like 49 is provided in the first end 48, while a second open pocket, configured opening, or the like 51 is provided in the second end 50.

Figure 12:
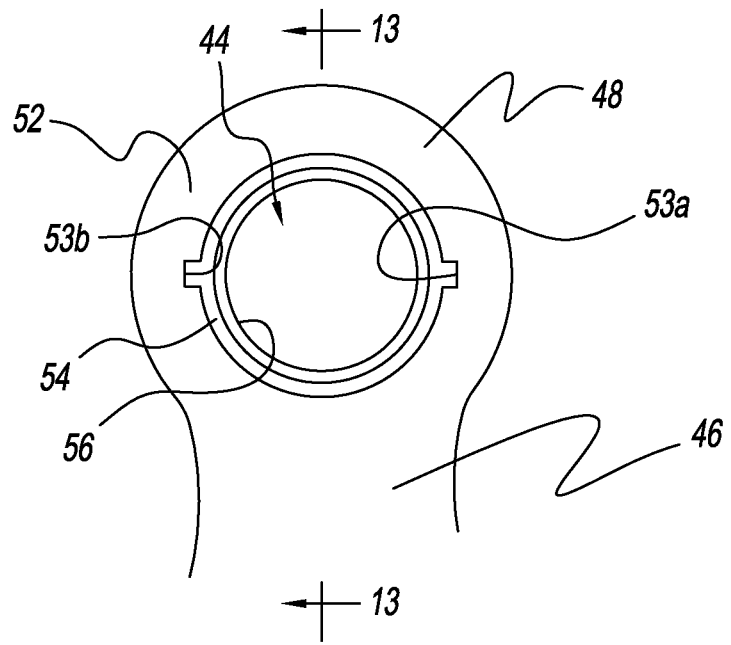
FIG. 12 is an enlarged top plan view of an end of the plate of the orthopedic implant of FIG. 9.

The first pocket 49 (see, e.g., FIGS. 9 and 12) has a generally conical inlet wall 52 with an annular slot 54 formed in the side wall 52 of the pocket 49, the annular undercut, slot or the like 54 forming a seat, ledge or the like to capture the insert 60 (see, e.g., FIG. 12). A first notch or keyway 53a is provided in the side wall 52 of the pocket 49 and in communication with the annular undercut 54. A second notch 53b is provided in the side wall 52 of the pocket 49 and is in communication with the annular undercut 54. The two keyways 53a, 53b provide for the pocket 49 to be keyed for the insert 60. In the current form, the keyways 53a, 53b are disposed diametrically opposite one another. It should be appreciated however, that the keyways 53a, 53b may be spaced differently as well as shaped differently and of different number. Preferably, but not necessarily, the keyways are spaced equidistant from one another about the undercut 54.

While not shown, the second pocket 51 of the body 44 has the same features and functions as the first pocket 49, including, but not limited to, a generally conical inlet wall with an annular slot formed in the side wall of the pocket 51, the annular undercut, slot or the like forming a seat, ledge or the like to capture the insert 60. A first notch or keyway is provided in the side wall of the pocket 51 and in communication with the annular undercut. A second notch is provided in the side wall of the pocket 51 and is in communication with the annular undercut. The two keyways 53a, 53b provide for the pocket 51 to be keyed for the insert 60. In the current form, the keyways 53a, 53b are disposed diametrically opposite one another. It should be appreciated however, that the keyways may be spaced differently as well as shaped differently and of different number. Preferably, but not necessarily, the keyways are spaced equidistant from one another about the undercut 54.

Figure 13:
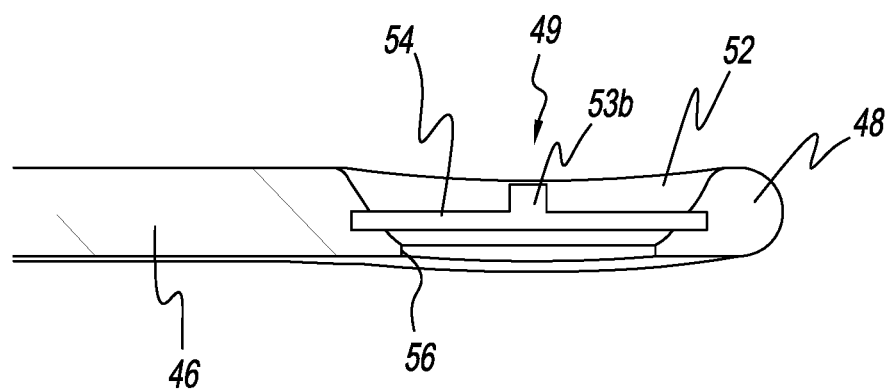
FIG. 13 is an enlarged side sectional view of the end of the plate of FIG. 12 taken along line 13-13 thereof.
Figure 14:
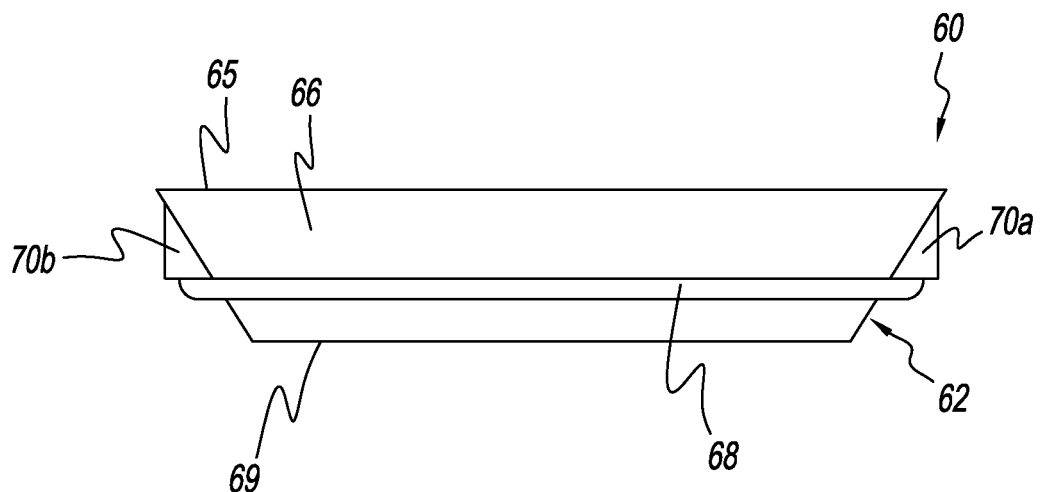
FIG. 14 is an enlarged side view of one side of the insert of the orthopedic implant of FIG. 15.
Figure 15:
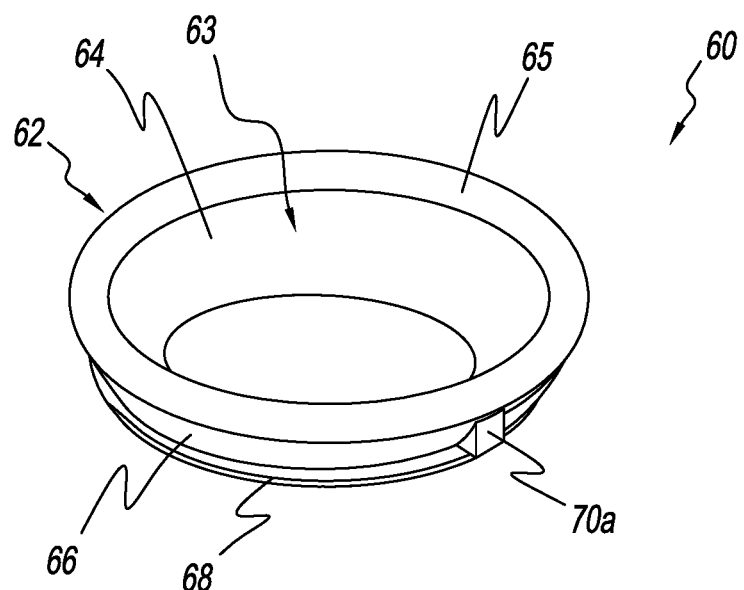
FIG. 15 is an isometric view of the insert of the orthopedic implant of FIG. 9.
Figure 16:
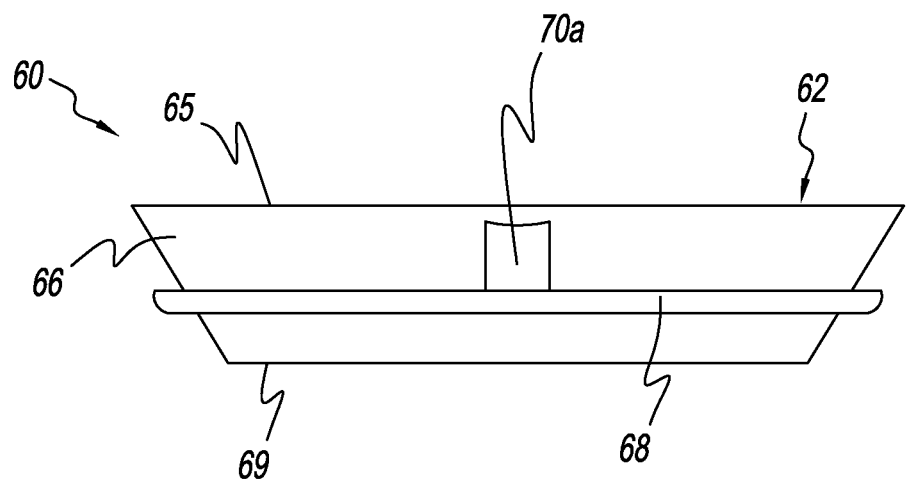
FIG. 16 is an enlarged side view of another side of the insert of the orthopedic implant of FIG. 15.

The underside of each pocket 49, 51 is configured as shown in FIG. 13 where the underside 56 of the pocket 49 is illustrated. The underside 56 is angled to receive threading of the bone screw 80a. This aids in locking the angle and position of the bone screw 80a relative to the plate 42.

The insert 60 is shown in greater detail in FIGS. 13-16 and reference is made thereto. The insert 60 is preferably, but not necessarily, made from PEEK but other materials may be used. The insert 60 is characterized by a generally round, annular body 62 defining an opening 63 having a generally conical side wall 64 and a flat, annular top 65. The body 62 is sized to fit into the pockets 48, 50 of the plate 42. The body 62 has a generally conical outer side wall 66 and a flat annular bottom 69. A race, ledge, projection or the like 68 is disposed along an outer circumference of the outer side wall 66 of the body 62 proximate the bottom 69. The race 68 abuts the annular slot of the pocket when the insert 60 is received in the pocket in order to prevent the insert 60 from dislodging from the screw pocket.

The insert is also keyed to fit into the keyed screw pocket to prevent rotation. A first projection or key 70a is provided in the outer side wall 66 of the body 62 and in communication with the race 68. A second projection or key 70b is provided in the outer side wall 66 of the body 62 and is in communication with the race 68. The two keys 70a, 70b provide for the insert 60 to be keyed to the pocket via its keyways 53a, 53b. In the current form, the keys 70a, 70b are disposed diametrically opposite one another. It should be appreciated however, that the keys may be spaced differently as well as shaped differently and of different number, corresponding to the shape, number and spacing of the keyways of the pocket. Preferably, but not necessarily, the keys are spaced equidistant from one another about the race 68 in like manner as the keyways of the pockets.

FIGS. 19 and 20 show the variable angle locking screw and plate implant 40 assembled with the inserts 60 situated in the pockets 49, 51 of the plate 42, with the variable angle locking screws 80a in the inserts 60. FIG. 20 is a sectional view of the assembled implant 40 that particularly shows the inserts 60 keyed into the pockets 49, 51 with the variable angle locking screws 80a locked into the inserts 60.

Figure 17:
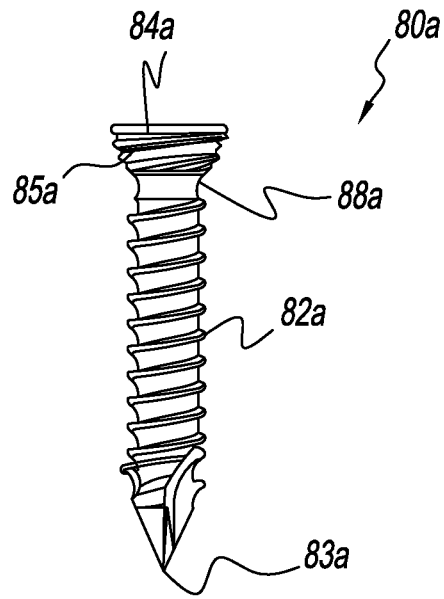
FIG. 17 is a side view of the variable angle locking screw of the orthopedic implant of FIG. 9.
Figure 18:
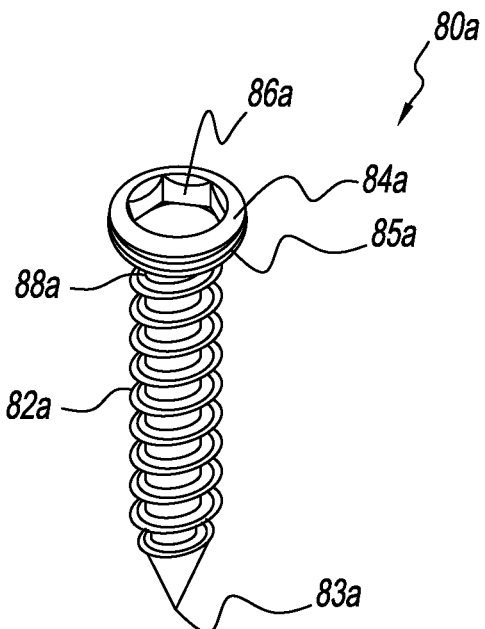
FIG. 18 is an isometric view of the variable angle locking screw of FIG. 17.

Referring to FIGS. 17 and 18, the variable angle locking bone screw 80a is shown. The variable angle locking bone screw 80a is characterized by a threaded shank 82a having a preferably, but not necessarily, pointed tip 83a at a distal end of the threaded shank 82a, a neck 88a at a proximate end of the threaded shank 82a, and a head 84a at the end of the neck 88a. A socket 86a is provided in the top of the head 84a that is configured to receive a like configured driving tool (not shown). While the socket 86a is configured as a hexagon for receipt of a hexagon driving tool (not shown), other socket configurations and thus driver tools may be used. The underside of the head 84a has dual threads or threading 85a. The dual threading underside 85a of the head 84a engages the insert 60 in a pocket of the plate 42 to angularly position and fix the screw 80a relative to the plate 42.

Figure 21:
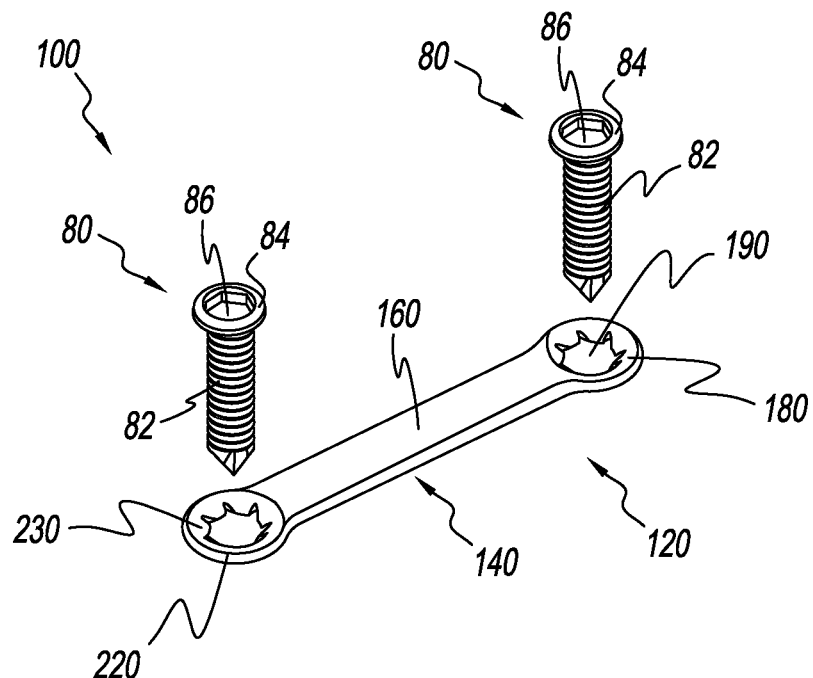
FIG. 21 is an exploded view of components of an orthopedic implant fashioned in accordance with the present principles.
Figure 22:
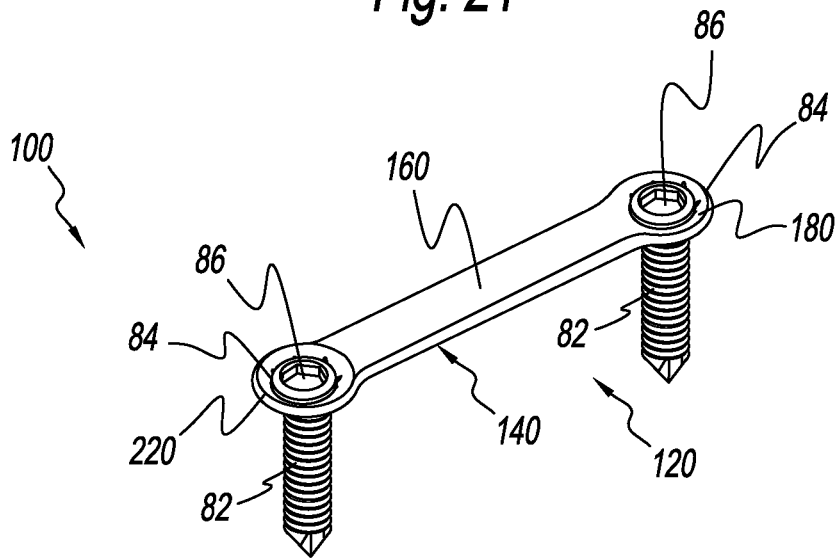
FIG. 22 is an isometric view of the orthopedic implant of FIG. 21, assembled.

Referring to FIGS. 21 and 22, there is depicted an exemplary form of the present orthopedic implant, construct, device or the like, generally designated 100, comprising two bone screws 80 and a plate 120 providing variable angle bone screw locking. The orthopedic implant 100 is made from a biocompatible material such as, but not limited to, titanium, stainless steel, an alloy of titanium or steel, or other biocompatible material, and is designed for use with various bones of the body such as, but not limited to, vertebrae of the spine. FIG. 21 shows the two (2) components of the orthopedic implant 100 namely, the configured bone screw 80 and a variable angle bone screw locking plate (plate) 120, in an exploded or unassembled state, while FIG. 21 depicts the components of the orthopedic implant 100 in an un-exploded or assembled state.

Figure 23:
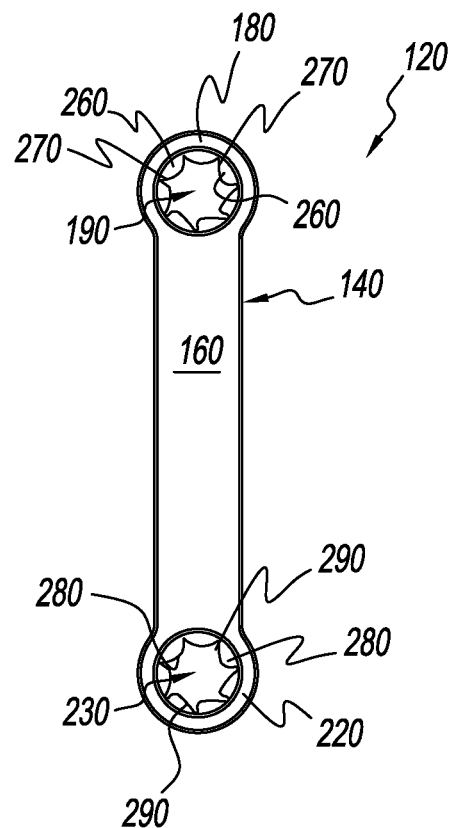
FIG. 23 is a top plan view of the plate of the orthopedic implant of FIG. 21.
Figure 24:
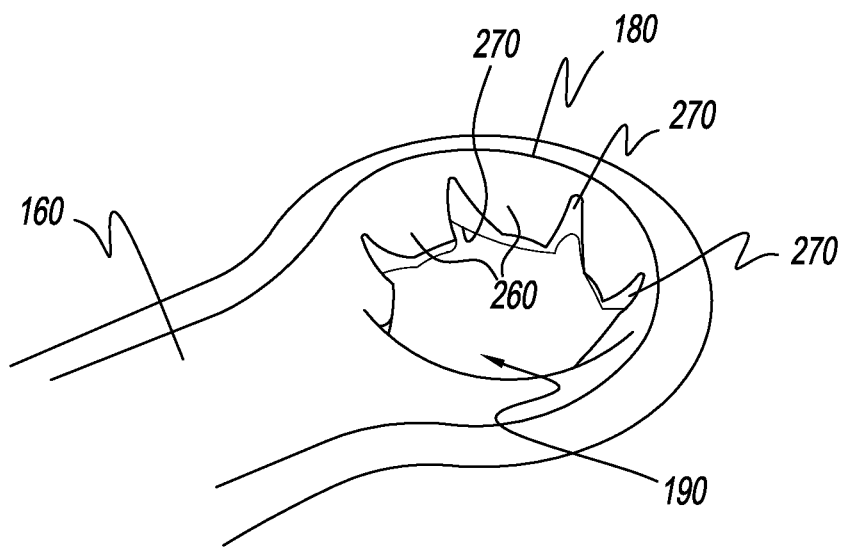
FIG. 24 is an enlarged view of one end/bone screw pocket of the plate of FIG. 23.
Figure 25:
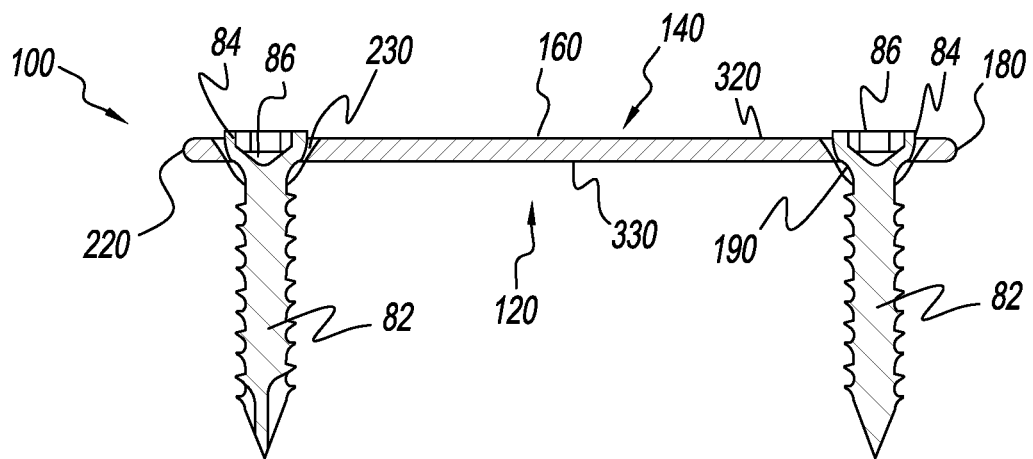
FIG. 25 is a sectional side view of the assembled orthopedic implant of FIG. 22.
Figure 26:
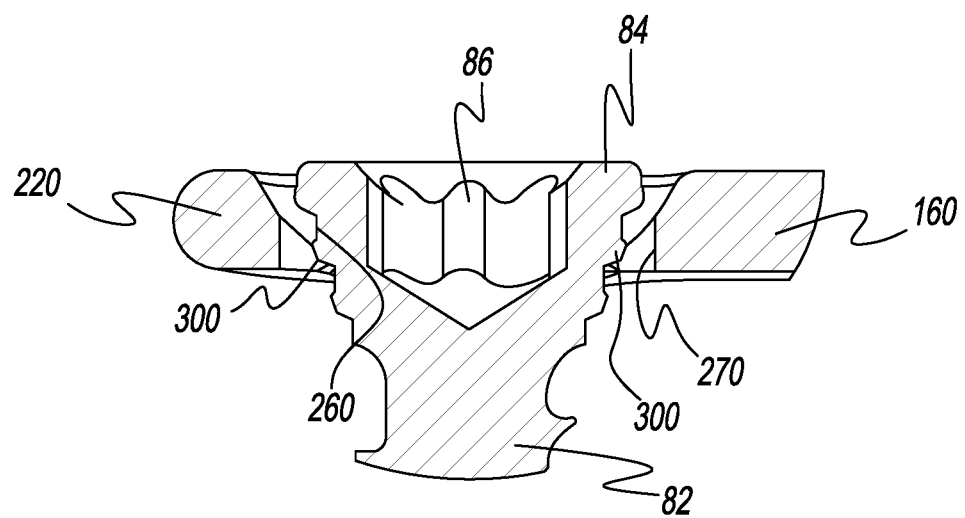
FIG. 26 is an enlarged sectional view of one end/bone screw pocket of the sectional side view of FIG. 25.

As seen in FIG. 23, the plate 120 is characterized by a generally elongated elliptical body 140 having a first rounded end 180 and a second rounded end 220, the nomenclature first and second being arbitrary here and throughout.

A strut 160 extends between the first rounded end 180 and the second rounded end 220. The body 140 is generally flat, having a generally flat upper side 320 and a generally flat lower side 330, but may have a curvature along the major axis or another long axis of the body 140 and/or along the minor axis or another short axis of the body 140. A first pocket, configured opening, or the like 190 is provided in the first end 180, while a second pocket, configured opening, or the like 230 is provided in the second end 220.

The first pocket 190 has a generally conical or cup-shaped inlet with a plurality of cutouts, slots or the like (cutouts) 270 formed about the lower periphery of the pocket opening 190. The plurality of cutouts 270 define a plurality of lips, tangs, ledges or the like (lips) 260. Each lip 260 has a generally rounded, curved or arched tip or end. Preferably, but not necessarily, the cutouts 270 are spaced equidistant from one another about the annular conical inlet, such that the lips 260 are likewise equidistant from one another. The number of cutouts 270 and lips 260 both odd and even are contemplated to be used. The second pocket 230 likewise has a generally conical or cup-shaped inlet with a plurality of cutouts, slots or the like (cutouts) 290 formed about the lower periphery of the pocket opening 230. The plurality of cutouts 290 define a plurality of lips, tangs, ledges or the like (lips) 280. Each lip 280 has a generally rounded, curved or arched tip or end. Preferably, but not necessarily, the cutouts are spaced equidistant from one another about the annular conical inlet, such that the formed lips 280 are likewise equidistant from one another. The number of cutouts 290 and lips 280 both odd and even are contemplated to be used. Preferably, but not necessarily, the number of cutouts and lips for each pocket 190, 230 are the same. These lips threadedly engage with the dual thread of the bone screw 80 (as described below), preventing the bone screw 80 from moving, thus locking the bone screw 80 into position relative to the pocket and thus the plate 120.

The underside of each pocket 190, 230 is configured as shown in FIG. 6 where the underside 300 of the pocket 230 of the second end 220 is illustrated. The underside 300 is angled to receive threading of the bone screw 80. This aids in locking the angle and position of the bone screw 80 relative to the plate 120.

Figure 27:
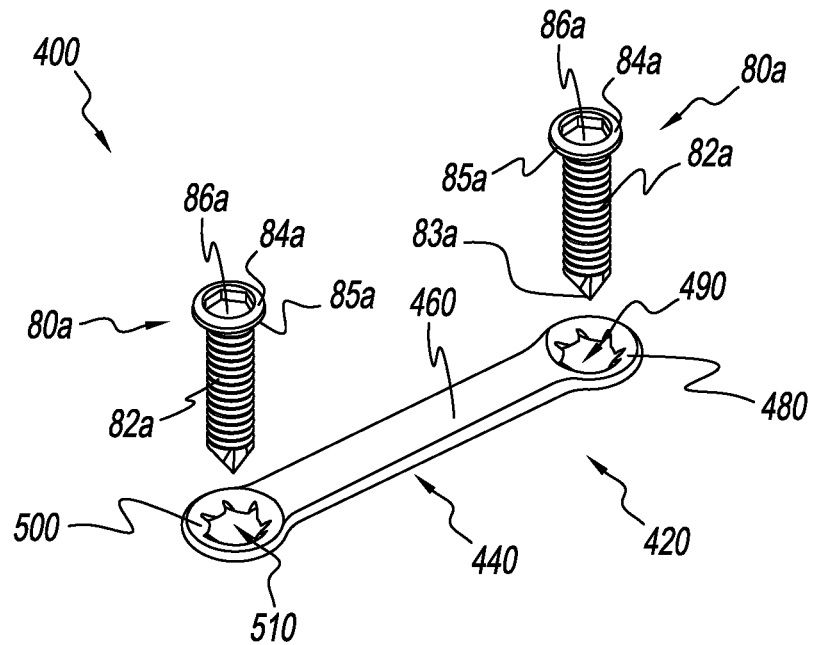
FIG. 27 is an exploded view of components of another orthopedic implant fashioned in accordance with the present principles.
Figure 28:
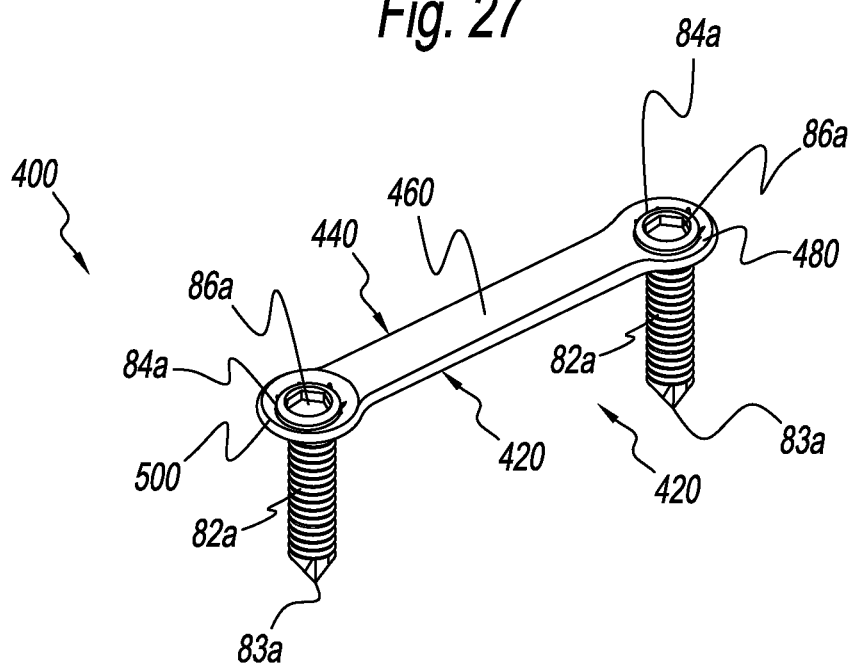
FIG. 28 is an isometric view of the orthopedic implant of FIG. 27, assembled.

Referring to FIGS. 27 and 28, there is depicted another exemplary form of the present orthopedic implant, construct, device or the like, generally designated 400, comprising two bone screws 80a and a plate 420 providing variable angle bone screw locking. The orthopedic implant 400 is made from a biocompatible material such as, but not limited to, titanium, stainless steel, an alloy of titanium or steel, or other biocompatible material, and is designed for use with various bones of the body such as, but not limited to, vertebrae of the spine. FIG. 27 shows the two (2) components of the orthopedic implant 400 namely, a configured bone screw 80a and a variable angle bone screw locking plate (plate) 420, in an exploded or unassembled state, while FIG. 28 depicts the components of the orthopedic implant 400 in an un-exploded or assembled state.

Figure 29:
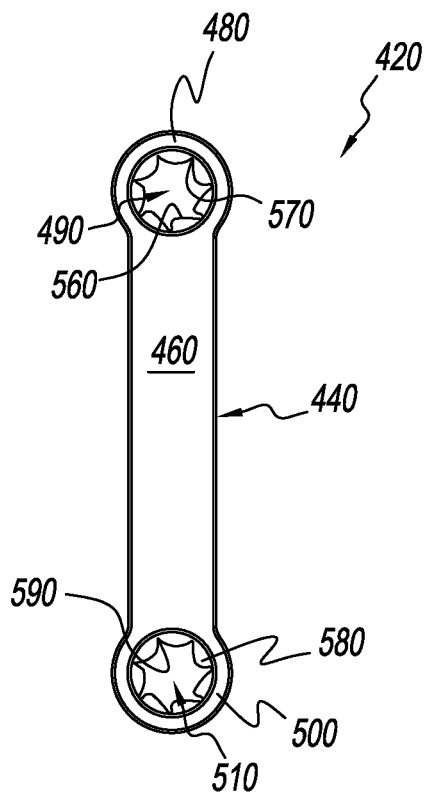
FIG. 29 is a top plan view of the plate of the orthopedic implant of FIG. 27.
Figure 30:
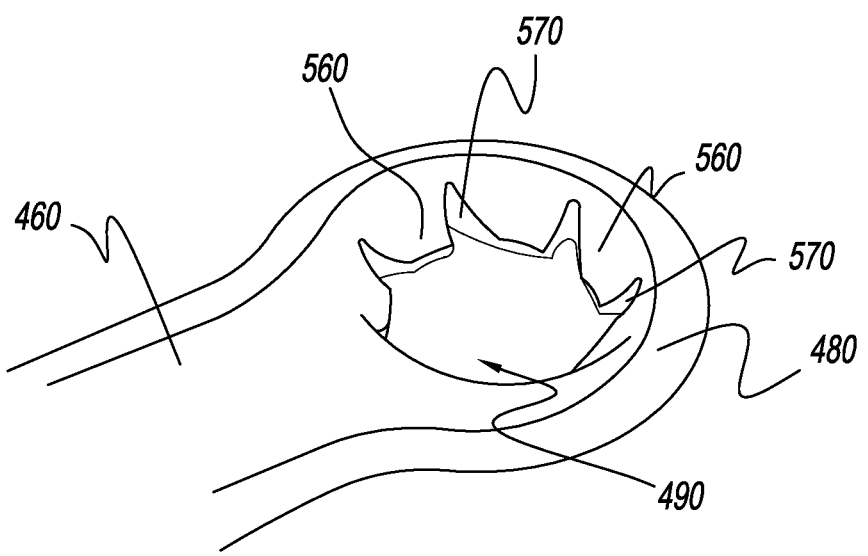
FIG. 30 is an enlarged view of one end/bone screw pocket of the plate of FIG. 29.
Figure 31:
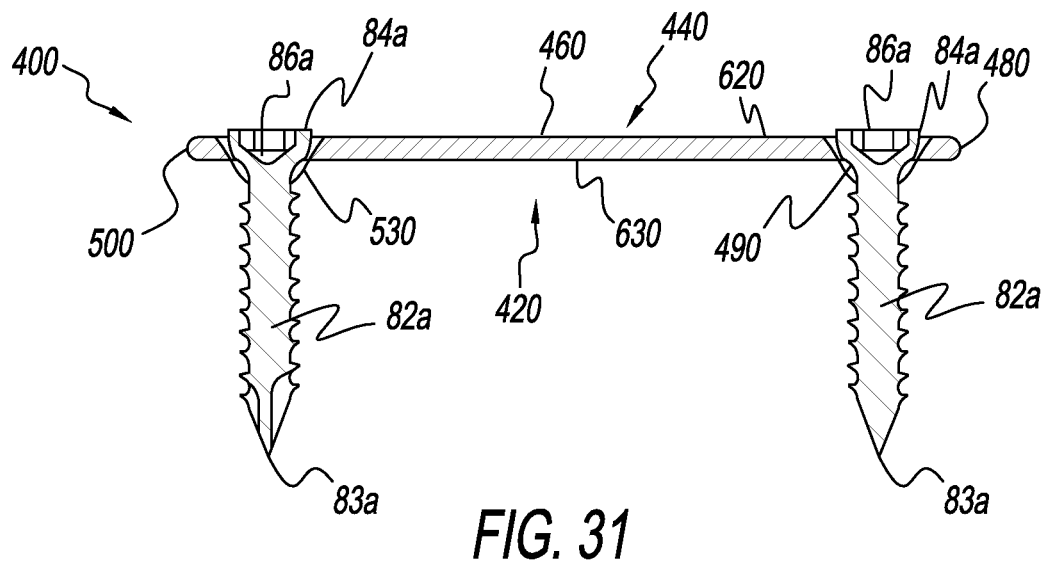
FIG. 31 is a sectional side view of the assembled orthopedic implant of FIG. 28.

As seen in FIG. 29, the plate 420 is characterized by a generally elongated elliptical body 440 having a first rounded end 480 and a second rounded end 500, the nomenclature first and second being arbitrary here and throughout. A strut 460 extends between the first rounded end 480 and the second rounded end 500. The body 440 is generally flat as best seen in FIG. 31, having a generally flat upper side 620 and a generally flat lower side 630, but may have a curvature along the major axis or another long axis of the body 440 and/or along the minor axis or another short axis of the body 440. A first pocket, configured opening, or the like 490 is provided in the first end 48, while a second pocket, configured opening, or the like 510 is provided in the second end 500.

The first pocket 490 has a generally conical or cup-shaped inlet with a plurality of cutouts, slots or the like (cutouts) 570 formed about the lower periphery of the pocket opening 490. The plurality of cutouts 570 define a plurality of lips, tangs, ledges or the like (lips) 560. Each lip 560 has a generally blunt, straight or flat tip or end. Preferably, but not necessarily, the cutouts 570 are spaced equidistant from one another about the annular conical inlet, such that the lips 560 are likewise equidistant from one another. The number of cutouts 570 and lips 560 both odd and even are contemplated to be used. The second pocket 510 likewise has a generally conical or cup-shaped inlet with a plurality of cutouts, slots or the like (cutouts) 590 formed about the lower periphery of the pocket opening 510. The plurality of cutouts 590 define a plurality of lips, tangs, ledges or the like (lips) 580. Each lip 580 has a generally blunt, straight or flat tip or end. Preferably, but not necessarily, the cutouts are spaced equidistant from one another about the annular conical inlet, such that the formed lips 580 are likewise equidistant from one another. The number of cutouts 590 and lips 580 both odd and even are contemplated to be used. Preferably, but not necessarily, the number of cutouts and lips for each pocket 490, 510 are the same. These lips threadedly engage with the dual thread of the bone screw 80a (as described below), preventing the bone screw 80a from moving, thus locking the bone screw 80a into position relative to the pocket and thus the plate 420.

Figure 32:
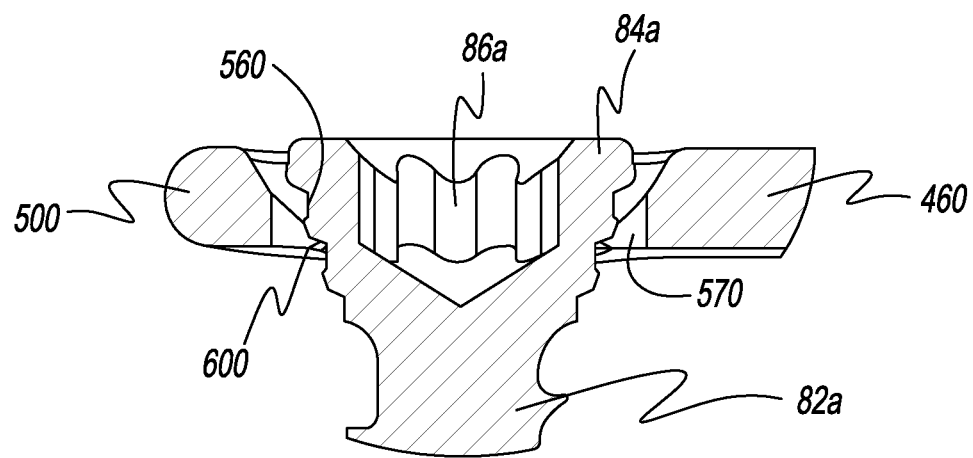
FIG. 32 is an enlarged sectional view of one end/bone screw pocket of the sectional side view of FIG. 31.

The underside of each pocket 490, 510 is configured as shown in FIG. 32 where the underside 600 of the pocket 510 of the second end 500 is illustrated. The underside 60 is angled to receive threading of the bone screw 80a. This aids in locking the angle and position of the bone screw 80a relative to the plate 420.

It should be appreciated that dimensions of the components, structures, and/or features of the present orthopedic implant can be altered as desired.

What is claimed is:

1. An orthopedic implant comprising:
   a plate having an upper surface, a lower surface, a first end, a second end, and a bone screw pocket at the first end, the bone screw pocket having a conical sidewall defining a bore extending through the plate from the upper surface to the lower surface, the conical sidewall having at least one keyway, wherein the at least one keyway of the conical sidewall includes a first keyway and a second keyway;
   an annular insert including at least one keyed projection, wherein the annular insert is configured to be disposed in the bone screw pocket, such that the at least one keyed projection engages the at least one keyway of the conical sidewall, and wherein the at least one keyed projection extends from the annular insert along a plane that is perpendicular to a central axis of the annular insert; and
   a bone screw having an externally threaded shaft and a head at an end of the externally threaded shaft, the bone screw is configured to be received in the annular insert and the bone screw pocket.

2. The orthopedic implant of claim 1, wherein the first keyway of the conical sidewall is disposed diametrically opposite the second keyway of the conical sidewall.

3. The orthopedic implant of claim 1, wherein the first keyway of the conical sidewall is a first shape and the second keyway of the conical sidewall is a second shape.

4. The orthopedic implant of claim 3, wherein the first shape of the first keyway of the conical sidewall is different than the second shape of the second keyway of the conical sidewall.

5. The orthopedic implant of claim 1, wherein the at least one keyed projection of the annular insert includes a first keyed projection and a second keyed projection.

6. The orthopedic implant of claim 5, wherein the first keyed projection of the annular insert is disposed diametrically opposite the second keyed projection of the annular insert.

7. The orthopedic implant of claim 1, wherein the at least one keyway of the conical sidewall includes a plurality of keyways.

8. The orthopedic implant of claim 7, wherein the plurality of keyways of the conical sidewall are spaced equidistant to each other.

9. The orthopedic implant of claim 1, wherein the at least one keyed projection of the annular insert includes a plurality of keyed projections that are spaced equidistant to each other.

10. The orthopedic implant of claim 1, wherein engagement between the at least one keyed projection of the annular insert and the at least one keyway of the conical sidewall is configured to prevent the annular insert from rotating relative to the bone screw pocket.

11. An orthopedic implant comprising:
a plate having an upper surface, a lower surface, a first end, a second end, and a bone screw pocket at the first end, the bone screw pocket having a conical sidewall defining a bore extending through the plate from the upper surface to the lower surface, the conical sidewall having an annular slot, wherein the conical sidewall further comprises at least one keyway;
an annular insert including a projection extending around a circumference of the annular insert, wherein the annular insert is configured to be disposed in the bone screw pocket such that the projection engages the annular slot of the conical sidewall, and wherein the projection extends from the annular insert along a plane that is perpendicular to a central axis of the annular insert, and wherein the annular insert includes at least one keyed projection, such that the at least one keyed projection engages the at least one keyway of the conical sidewall; and
a bone screw having an externally threaded shaft and a head at an end of the externally threaded shaft, the bone screw is configured to be received in the annular insert and the bone screw pocket.

12. The orthopedic implant of claim 11, wherein the annular slot of the conical sidewall is in communication with the at least one keyway of the conical sidewall.

13. The orthopedic implant of claim 11, wherein the projection of the annular insert is in communication with the at least one keyed projection of the annular insert.

14. The orthopedic implant of claim 11, wherein the head of the bone screw further includes a threading on the underside of the head configured to be disposed in the annular insert, such that the threading of the head engages the annular insert.

15. The orthopedic implant of claim 11, wherein engagement between the projection of the annular insert and the annular slot of the conical sidewall is configured to prevent the annular insert from being dislodged from the bone screw pocket.

16. An orthopedic implant comprising:
a plate having an upper surface, a lower surface, and a bone screw pocket, the bone screw pocket having a conical sidewall and an annular slot, the conical wall defining a bore extending through the plate from the upper surface to the lower surface;
an annular insert configured to be disposed in the bone screw pocket; and
a bone screw having an externally threaded shaft and a head at an end of the externally threaded shaft, the bone screw is configured to be received in the annular insert and the bone screw pocket;
wherein the annular insert is prevented from rotating relative to the bone screw pocket by an engagement between an at least one keyed projection and an at least one keyway, wherein the at least one keyed projection extends from the annular insert along a plane that is perpendicular to a central axis of the annular insert;
wherein the annular insert is prevented from being dislodged from the bone screw pocket by an engagement between a projection extending around a circumference of the annular insert and the annular slot.

17. The orthopedic implant of claim 16, wherein the annular insert includes the at least one keyed projection, and the conical sidewall includes the at least one keyway.

18. The orthopedic implant of claim 16, wherein the annular insert includes the projection, and the conical sidewall includes the annular slot.

19. An orthopedic implant comprising:
a plate having an upper surface, a lower surface, a first end, a second end, and a bone screw pocket at the first end, the bone screw pocket having a conical sidewall defining a bore extending through the plate from the upper surface to the lower surface, the conical sidewall having an annular slot;
an annular insert including a projection extending around a circumference of the annular insert, wherein the annular insert is configured to be disposed in the bone screw pocket such that the projection engages the annular slot of the conical sidewall, and wherein the projection extends from the annular insert along a plane that is perpendicular to a central axis of the annular insert; and
a bone screw having an externally threaded shaft and a head at an end of the externally threaded shaft, the bone screw is configured to be received in the annular insert and the bone screw pocket, wherein the head of the bone screw further includes a threading on the underside of the head configured to be disposed in the annular insert, such that the threading of the head engages the annular insert.

20. The orthopedic implant of claim 19, wherein engagement between the projection of the annular insert and the annular slot of the conical sidewall is configured to prevent the annular insert from being dislodged from the bone screw pocket.

* * * * *